US010775359B2

(12) United States Patent
Jones et al.

(10) Patent No.: US 10,775,359 B2
(45) Date of Patent: Sep. 15, 2020

(54) MEASUREMENT OF FORMATION ROCK PROPERTIES BY DIFFUSION

(71) Applicant: Halliburton Energy Services, Inc., Houston, TX (US)

(72) Inventors: Christopher Michael Jones, Katy, TX (US); Louis W. Elrod, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 427 days.

(21) Appl. No.: 15/074,315

(22) Filed: Mar. 18, 2016

(65) Prior Publication Data

US 2016/0202230 A1 Jul. 14, 2016

Related U.S. Application Data

(63) Continuation of application No. 13/408,655, filed on Feb. 29, 2012, now abandoned, which is a continuation of application No. 11/418,669, filed on May 5, 2006, now abandoned.

(51) Int. Cl.
*G01N 33/24* (2006.01)
*G01N 15/08* (2006.01)
(52) U.S. Cl.
CPC ......... *G01N 33/24* (2013.01); *G01N 15/0806* (2013.01); *G01N 15/088* (2013.01); *G01N 33/241* (2013.01)
(58) Field of Classification Search
None
See application file for complete search history.

(56) References Cited

U.S. PATENT DOCUMENTS

2007/0259433 A1 11/2007 Jones et al.
2012/0160018 A1 6/2012 Jones et al.

OTHER PUBLICATIONS

"U.S. Appl. No. 11/418,669, Appeal Brief filed Jan. 28, 2011", 15 pgs.
"U.S. Appl. No. 11/418,669, Examiner Interview Summary dated Feb. 14, 2012", 3 pgs.
"U.S. Appl. No. 11/418,669, Final Office Action dated Mar. 29, 2010", 6 pgs.
"U.S. Appl. No. 11/418,669, Final Office Action dated Aug. 30, 2011", 8 pgs.
"U.S. Appl. No. 11/418,669, Non Final Office Action dated Mar. 16, 2011", 9 pgs.
"U.S. Appl. No. 11/418,669, Non-Final Office Action dated Jun. 15, 2009", 9 pgs.
"U.S. Appl. No. 11/418,669, Notice of Non-Compliant Amendment dated Feb. 12, 2010", 6 pgs.
"U.S. Appl. No. 11/418,669, Response filed Feb. 18, 2010 to Notice of Non-Compliant Amendment dated Feb. 12, 2010", 6 pgs.
"U.S. Appl. No. 11/418,669, Response filed Jul. 7, 2011 to Non-Final Office Action dated Mar. 16, 2011", 12 pgs.

(Continued)

*Primary Examiner* — Xiaoyun R Xu
(74) *Attorney, Agent, or Firm* — Gilliam IP PLLC

(57) ABSTRACT

Embodiments of the present invention relate to a method to determine formation measurements, the method comprising placing a sample in a reservoir, removing aliquots from the reservoir containing the sample or continuously monitoring the reservoir or headspace as the sample and reservoir equilibrate and analyzing the aliquots or readings sufficient to provide diffusion measurements.

21 Claims, 6 Drawing Sheets

(56) References Cited

OTHER PUBLICATIONS

"U.S. Appl. No. 11/418,669, Response filed Dec. 15, 2009 to Non Final Office Action dated Jun. 15, 2009", 10 pgs.
"U.S. Appl. No. 13/408,655, Appeal Brief filed Jul. 29, 2013", 34 pgs.
"U.S. Appl. No. 13/408,655, Appeal Decision dated Jan. 19, 2016", 9 pgs.
"U.S. Appl. No. 13/408,655, Final Office Action dated Mar. 20, 2013", 8 pgs.
"U.S. Appl. No. 13/408,655, Non Final Office Action dated Jun. 12, 2012", 8 pgs.
"U.S. Appl. No. 13/408,655, Non Final Office Action dated Dec. 13, 2012", 7 pgs.
"U.S. Appl. No. 13/408,655, Pre-Appeal Brief Request for Review dated Jun. 3, 2013", 5 pgs.
"U.S. Appl. No. 13/408,655, Response filed May 28, 2012 to Restriction Requirement dated May 2, 2012", 8 pgs.
"U.S. Appl. No. 13/408,655, Response filed Dec. 3, 2012 to Non Final Office Action dated Jun. 12, 2012", 14 pgs.
"U.S. Appl. No. 13/408,655, Resriction Requirement dated May 2, 2012", 5 pgs.
"U.S. Appl. No. 13/408,655, Response filed Mar. 8, 2013 to Non Final Office Action dated Dec. 13, 2012", 12 pgs.
Loon, et al., "Evidence for a Second Transport Porosity for the diffusion of Tritiated Water (HTO) in a sedimentary rock (Opalinus Clay—OPA): Application of Through-and-Out diffusion Techniques", Transport in Porous Media, vol. 61, (2005), 193-214 pgs.
O'Hira, S., et al., "Tritium Safety-Related Studies at TPL of JAERI", Journal of Fusion Energy, vol. 16(3), (1997), 219-224 pgs.
Rees, K.C.J, "Evaluation of laboratory techniques for measuring diffusion coefficients in sediments", Environ. Sci. Technol., vol. 25(9),, (1991), 1605-1611.

MEASUREMENT OF FORMATION ROCK PROPERTIES BY DIFFUSION

CROSS REFERENCE TO RELATED APPLICATION

This application is a continuation application of U.S. patent application Ser. No. 13/408,655, filed Feb. 29, 2012, which application is a continuation application of U.S. patent application Ser. No. 11/418,669, filed May 5, 2006, which applications are incorporated by reference in their entirety and made a part hereof.

FIELD OF TECHNOLOGY

Embodiments of the present invention relate to the measurement of formation rock properties by diffusion. Specifically, embodiments of the present invention relate to the measurement of porosity and permeability for application in the oilfield industry.

BACKGROUND OF INVENTION

Diagnosing the structure of porous materials is relevant to a broad range of scientific and technological problems. Knowledge of the fluid transport properties of reservoir rocks is important for the monitoring of contaminant levels in reservoir rock samples and for information related to extracting oil, such as in determining oil well value and characterizing formations for making real-time or near real-time decisions in drilling. Understanding porosity and permeability is important for determining the quantity and producibility of hydrocarbons in a reservoir system. These data can impact reserves estimates as well as production and development planning.

Two of the most important parameters used to characterize porous materials are permeability and effective porosity. Permeability is a measure of the ability of a rock to transmit fluid through pore spaces. Effective porosity describes the interconnected pore volume or void space in a rock that contributes to fluid flow or permeability in a reservoir. Effective porosity excludes isolated pores and pore volume occupied by water adsorbed on clay minerals or other grains.

Porosity and permeability measurements are readily measured with existing techniques, but are usually measured separately and the methods can be invasive, toxic, or both. Effective porosity is also difficult to measure directly utilizing current techniques.

BRIEF DESCRIPTION OF THE DRAWINGS

Embodiments of the invention may be best understood by referring to the following description and accompanying drawings which illustrate such embodiments. In the drawings.

DETAILED DESCRIPTION OF THE EMBODIMENTS OF THE PRESENT INVENTION

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. The embodiments of the present invention relate the measurement of formation rock properties by diffusion.

Figure 1:
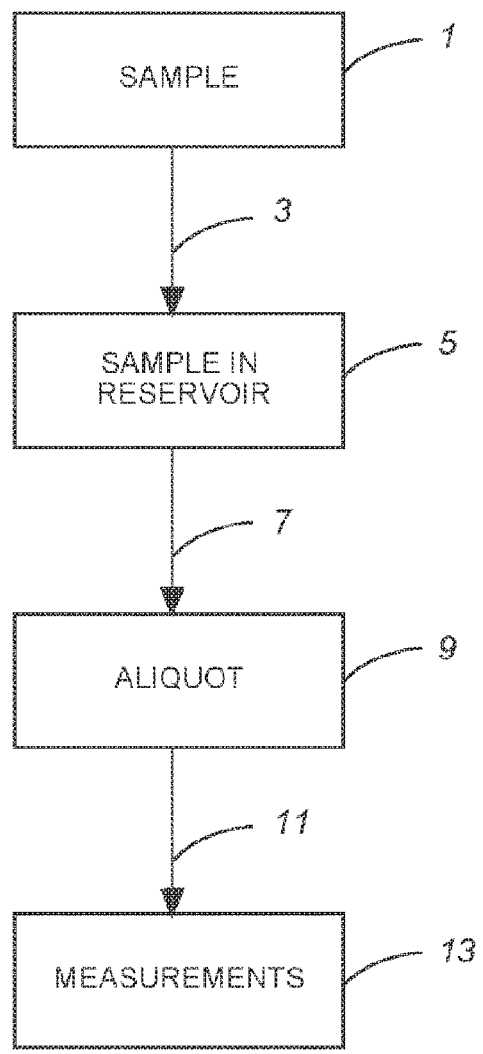
FIG. 1 illustrates a block flow diagram describing the measurement of formation rock properties by diffusion, according to some embodiments of the invention.

Referring to FIG. 1, a method to provide formation measurements by diffusion is shown, according to some embodiments of the invention. A sample (1) may be placed (3) in a reservoir (5). While the reservoir and sample are equilibrating, an aliquot (9) may be removed (7) for analysis (11), providing formation measurements (13).

Figure 2:
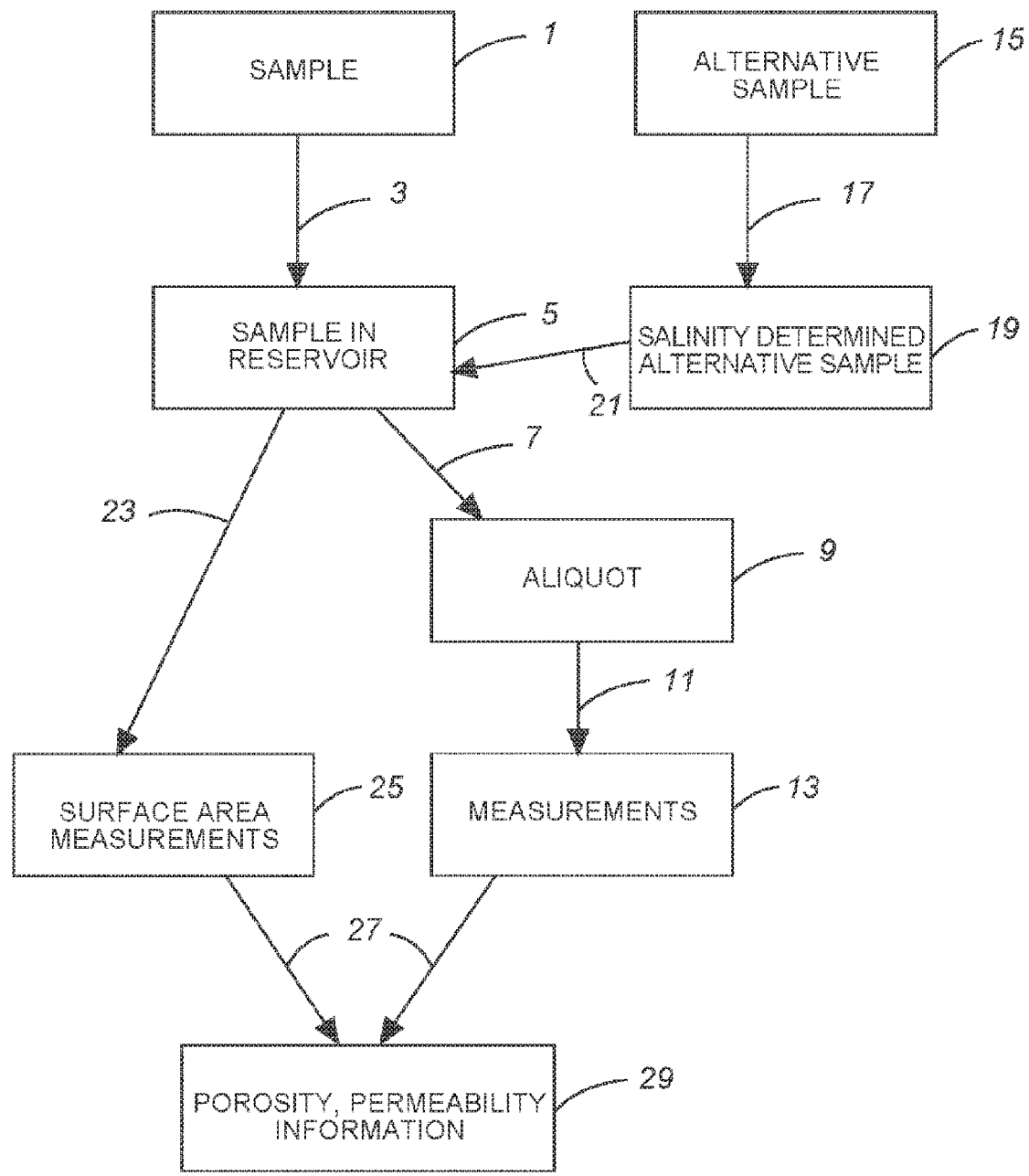
FIG. 2 illustrates a block flow diagram describing the measurement of porosity and permeability properties by diffusion, according to some embodiments of the invention.

Referring to FIG. 2, a method to provide porosity and permeability measurements by diffusion is shown, according to some embodiments of the invention. An alternative sample (15) is analyzed (17) to determine its salinity (19). The salinity determined alternative sample (19) is then used to adjust the salinity of the reservoir (21) to match any samples (1). A sample (1) is placed in the reservoir (3) in which the salinity has been adjusted (5). While the reservoir and sample are equilibrating, aliquots (9) may be removed (7). The aliquots are analyzed (11) for diffusion measurements (13). The sample is removed to determine surface area (23). The surface area measurements (25) and diffusion measurements (13) are used to calculate formation information (27), such as porosity and permeability (29).

Figure 3:
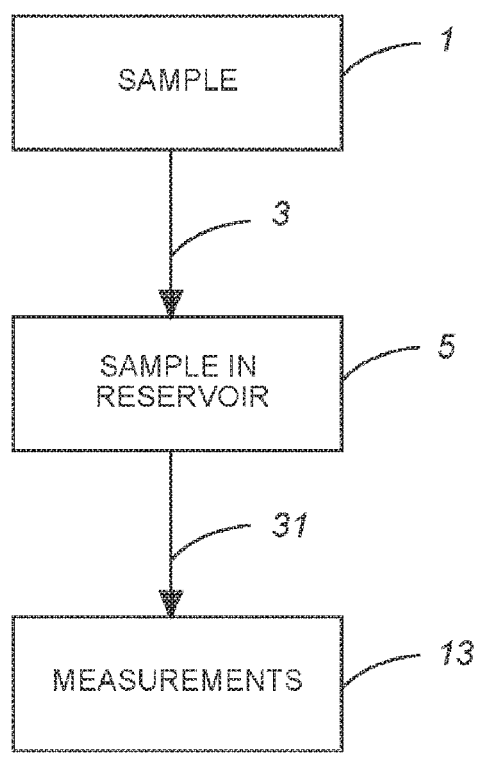
FIG. 3 illustrates block flow diagram describing the continuous measurement of formation rock properties by diffusion, according to some embodiments of the invention.

Referring to FIG. 3, a method to provide continuous formation measurements by diffusion is shown, according to some embodiments of the invention. A sample (1) may be placed (3) in a reservoir (5). While the reservoir and sample are equilibrating, continuous analysis is performed (31), providing formation measurements (13).

Figure 4:
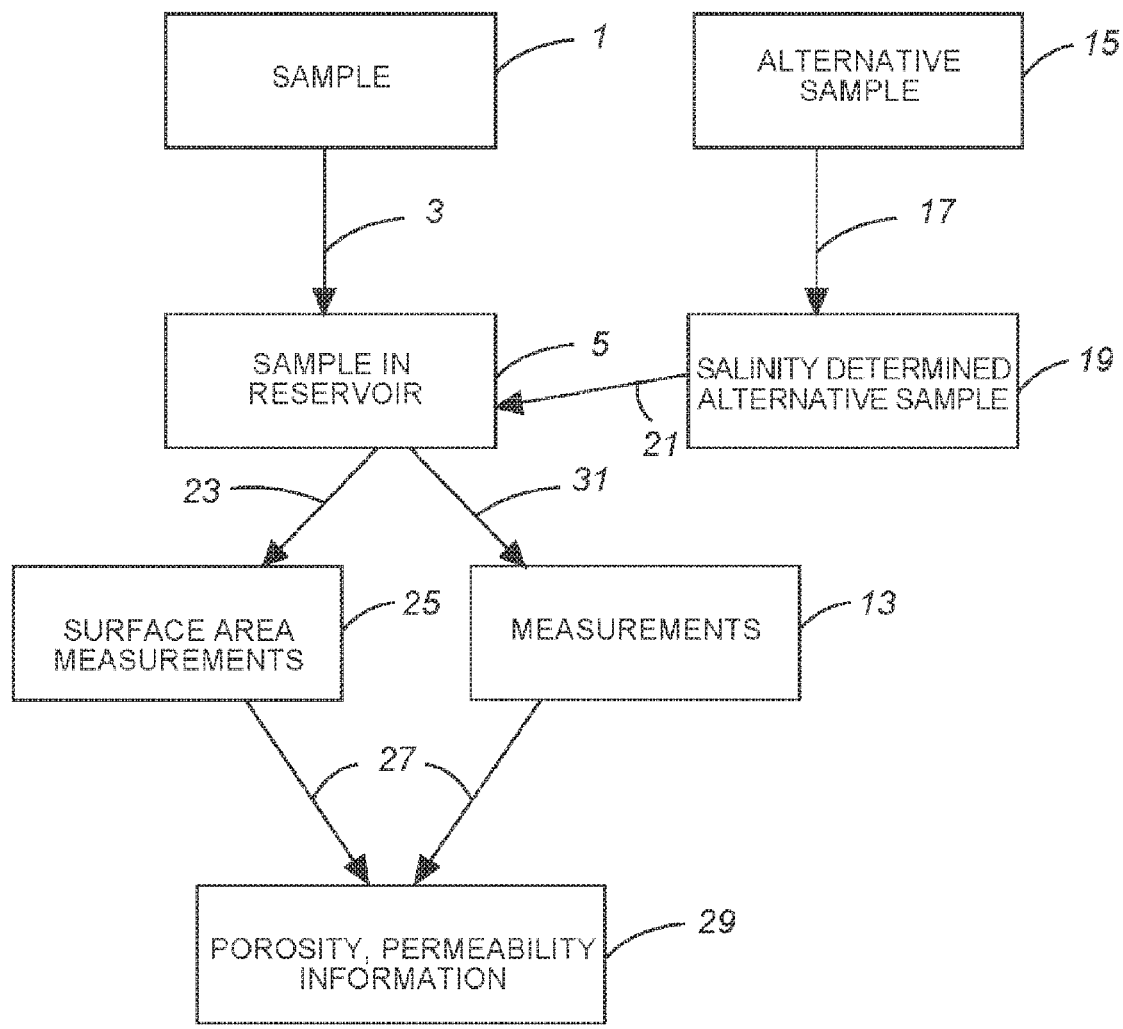
FIG. 4 illustrates a block flow diagram describing the continuous measurement of porosity and permeability properties by diffusion, according to some embodiments of the invention.

Referring to FIG. 4, a method to provide continuous porosity and permeability measurements by diffusion is shown, according to some embodiments of the invention. An alternative sample (15) is analyzed (17) to determine its salinity (19). The salinity determined alternative sample (19) is then used to adjust the salinity of the reservoir (21) to match any samples (1). A sample (1) is placed in the reservoir (3) in which the salinity has been adjusted (5). While the reservoir and sample are equilibrating, continuous analysis is performed (31), providing diffusion measurements (13). The sample is removed to determine surface area (23). The surface area measurements (25) and diffusion measurements (13) are used to calculate formation information (27), such as porosity and permeability (29).

Figure 5:
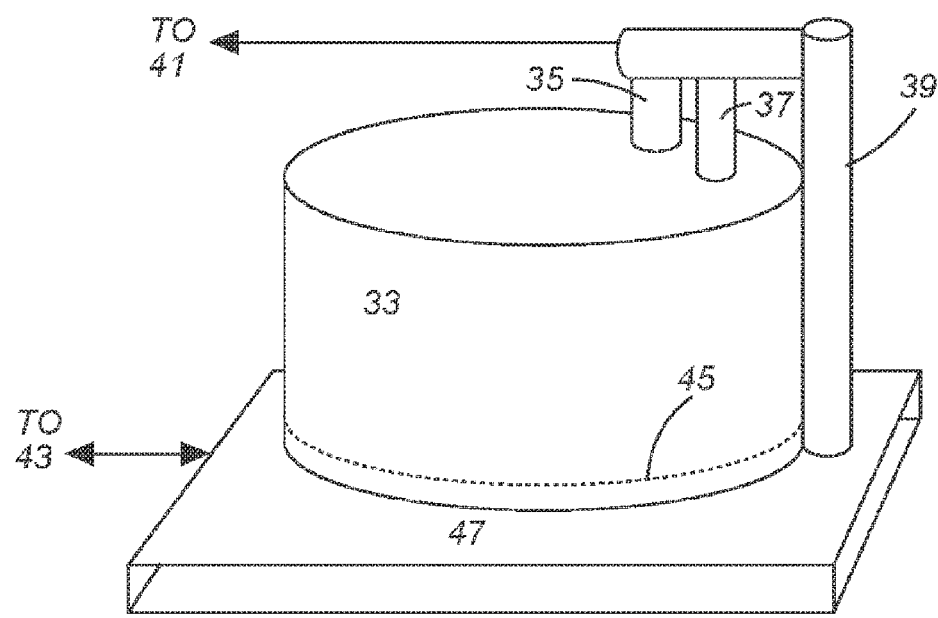
FIG. 5 illustrates a perspective view of an apparatus to measure formation rock properties by diffusion, according to some embodiments of the invention.

Referring to FIG. 5, an apparatus to provide formation measurements by diffusion is shown. A reservoir (33) may be coupled to an injection port (35). The reservoir (33) may be further coupled to a sampler (37). An agitator (47) may be positioned adjacent to the reservoir (33). An instrument for analysis (41) may be coupled to the sampler (37). Optionally, an automatic fluid titrator (39) may be coupled to the reservoir (33). A screen (45) may also be positioned near the bottom of the reservoir (33). A computer (43) may optionally be coupled to any one or combination of the sampler (37), instrument for analysis (41), automatic fluid titrator (39), injection port (35), agitator (47) and reservoir (33).

Referring to FIGS. 1-4, methods to determine formation measurements by diffusion are shown, according to some embodiments of the invention. A sample (1) is collected and placed (3) in a reservoir (5). In some embodiments, sample (1) refers to a representative portion of a whole. Further, sample (1) may be defined as a small segment or quantity taken as evidence of the quality or character of the entire group or lot. Examples of samples may be in liquid, solid or gas form, and in the oilfield industry, taken from the cuttings or core. Further examples of samples include any rock samples of sufficient size including core chips, core trim, sidewall cores, and outcrop samples. Cuttings refer to rock particles brought to the surface in well drilling. Core refers to a cylindrical sample of rock retrieved from a well. The cuttings or core may be rinsed of drilling or coring fluid and, if cuttings, may be sieved to an appropriate mesh size. In some embodiments, mesh size refers to one of the openings between the threads, cords or wires of a screen or net. Mesh size is often used to designate a size of screen or of the material passed by a screen in terms of the number of such openings per linear inch. Sieving may refer to separating or separating out by putting through a sieve or sifter or meshed material.

An alternative sample (15) is used to determine the salinity (17) of the target sample (1) by various techniques used in the industry. In some embodiments, salinity refers to a concentration of salt. The alternative sample (15) may be cuttings or core and preferably collected simultaneously or near in time and place to the target sample (1). Salinity is important to maintain because changes in salinity may affect porosity and permeability measurements of a sample (1). Effort must be taken to retain the salinity in the sample while allowing water to freely exchange between the sample and reservoir. For example, fresh water may swell clay samples, destroying both porosity and permeability.

One method to maintain salinity may be to use a semi-permeable membrane placed between the sample (1) and reservoir (33). An undesirable effect may be that osmotic pressure builds at the interface. Therefore, the osmotic pressure could be monitored and mathematically-experimentally accounted for or the pressure could be balanced by adjusting the salinity of the reservoir side of the interface. A quick titration could be performed until osmotic pressures balance and then measurements could be carried out. A saline addition to the reservoir side of the interface could be prepared ahead of time by matching the expected salinity of the sample (1) with information derived from the alternative sample (15). With the addition prepared ahead of time, an already quick titration could be sped up and minimize the time of any errors due to the short time of osmotic imbalance. An advantage of using a semi-permeable membrane is that only salinity need be matched without regard to the specific water composition. A semi-permeable membrane may work better in dealing with a core sample rather than cuttings.

Salinity may also be matched without the use of a semi-permeable membrane. If no membrane is used and only salinity is matched, the cations of the reservoir solution may exchange with the cations at the surface of the sample, which may change the sample properties. This effect may be negligible, but should be considered. To remedy such an effect, one skilled in the art could use an ion that is more soluble than other ions. By matching the salinity with this ion, it ensures that the salinity-matching ion will not exchange with ions on the surface of the sample. For example, cesium may be such an ion.

Another technique to regulate the salinity of the reservoir may be to mimic the properties of the target sample in the reservoir solution, using pre-measurements of an alternative sample (15). Formation water (sample water) generally conforms to a few expected patterns. With some pre-measurements of an alternative sample (15), the reservoir could be titrated to match the salinity of the sample to a reasonable degree of accuracy. All sample pre-measurements, titration, salinity calculations and osmotic measurements could be automated.

Once the salinity determining technique has been performed, the sample in reservoir (5) is optionally agitated to assist in equilibrating the sample and reservoir. The agitator may be a stirrer or more specifically, a magnetic stirrer. If a porous body saturated with fluid, such as a cuttings or core sample, is placed into a solution that is miscible with the saturation fluid, the fluids will exchange on a molecular level driven by diffusion even in the absence of any fluid potential. In some embodiments, diffusion refers to the random motion of molecules in a liquid or gas (or, very slowly, in a solid). The exchange will continue until equilibrium is reached with a rate described as an exponential process with respect to time.

Frick's Law describes diffusion by the equation $dq/dt = -DS(dc/dx)$ where q is the change in quantity of the substance, D is the diffusion constant, S is the surface area, c is the concentration of the substance, x is the distance it migrates and t is the time involved. Frick's Law explains that diffusion is proportional to the surface area of a porous material. Further, the diffusion constant described in Frick's Law is dependent on both fluid and medium properties.

Fluid properties may be subdivided into solute and solution properties. The diffusion constant for a solute is higher at higher temperatures and lower for particles of higher mass. Another important solute property is characterized as the interaction of the solute particle with the medium of interest, called solute and medium (SAM) interaction. For example, the SAM interaction may be high for an organic molecule on a clay surface, but low for an uncharged silver colloid particle of equal mass. As opposed to solute properties, the main solution property of interest is viscosity, in which the diffusion constant depends. The viscosity may be referred to as a fluid's internal resistance to motion. The diffusion constant is inversely proportional to the fluid viscosity and particle radius. Since most fluids' viscosity is a function of temperature, the temperature effect of diffusion to a higher order will be nonlinear.

Properties of the porous medium may be the SAM interactions mentioned, as well as the critical pore size. The critical pore size may be defined as the average of the largest openings connecting pores of a medium along a continuous path, also called the pore throat. Generally, the pore throat is the critical parameter of permeability. In some embodiments, permeability refers to the property of a porous material that is measured by the rate by volume at which a fluid of unit viscosity passes through unit cross section of the material under unit pressure gradient.

The rate of decrease in the amount of substance is proportional to a concentration gradient throughout the porous medium, the surface area of the porous medium exposed to the fluid, and the diffusion constant. Therefore, as the total reservoir concentration decreases, the rate of diffusion decreases. If one skilled in the art were to monitor the concentration of particles in the reservoir, an exponential decrease would be observed over time. The concentration may be monitored (11) by removing (7) small aliquots (9) from the sample in reservoir (5) as equilibrium is being established. Aliquot may refer to a portion of a solution. In some embodiments, equilibrium refers to the state in which the forward and reverse rates of all diffusion processes are equal, so that the concentrations of all species remain constant. Alternatively, a probe may be used to monitor (31) the concentration in the reservoir continuously or intermittently without removing a portion of the sample (1), as shown in FIGS. 3 and 4.

The concentration may be analyzed or monitored using an analysis instrument. The concentration may be measured in the reservoir solution or in the headspace of a closed container, for example. The analysis instrument may utilize spectroscopy, for example. In some embodiments, spectroscopy refers to the science that deals with the interactions of various types of radiation with matter. A radiation source first interacts with a sample. A detector then records the type of interaction, such as absorbance, transmittance or emission. The electrical signals from the detector are converted to useful numbers or a visual display such as a spectrum. Specifically, laser spectroscopy may be employed and refers to spectroscopy in which a laser is utilized as the source of radiation. Laser is an acronym for light amplification by stimulated emission of radiation. Examples of types of spectroscopy devices used may include Fourier Transform Infrared Spectrometers (FTIR) and Tunable Diode Laser Spectrometers (TDLS). In some embodiments, spectrometer refers to an instrument that provides information about the intensity of radiation as a function of wavelength or frequency. The concentration may be monitored by detecting an isotopic species in the reservoir. In some embodiments, isotopic species refers to a detectable isotope used to track a process or analyze a sample. For example, deuterated water or $^{18}O$ labeled water could be the isotopic species detected in the reservoir. Alternatively, specific ions may be detected by the analysis instrument, such as cesium iodide or cesium bromide salt.

As concentration is monitored, it approaches a constant value asymptotically. Either the doped species or its residual may be monitored in the reservoir. This value can be extrapolated without waiting for a final equilibrium to be reached. The extrapolated concentration is the concentration that would be achieved if the reservoir were diluted with the volume of fluid in the pore space. Assuming the initial concentration of particles in the sample is zero, the concentration of particles at equilibrium can be found by using the following equation: $C_e=C_I*V_R/(V_R+V_M)$ where $C_e$ is the equilibrium concentration, $C_I$ is the initial concentration of the reservoir, $V_R$ is the volume of the reservoir and $V_M$ is the volume of the medium. Because only the interconnected pore space is filled with particles of solute, it is the effective porosity that is measured. In some embodiments, porosity refers to the ratio of the volume of interstices of a material to the volume of its mass. Effective porosity may be defined as the interconnected pore volume or void space in a rock that contributes to fluid flow or permeability in a reservoir. Effective porosity excludes isolated pores and pore volume occupied by water adsorbed on clay minerals or other grains. Total porosity is the total void space in the rock whether or not it contributes to fluid flow. Effective porosity is typically less than total porosity. In addition, because solute particles generally only exchange with a miscible phase, it is only the volume of effective pore space occupied by a miscible phase that is measured. For example, if oil and water are present or if oil, water and gas are present, it will only be the volume occupied by the water that is measured. If the effective pore space is measured by saturation of the media with a single phase then both the true effective pore space and water saturation can be determined.

Figure 6:
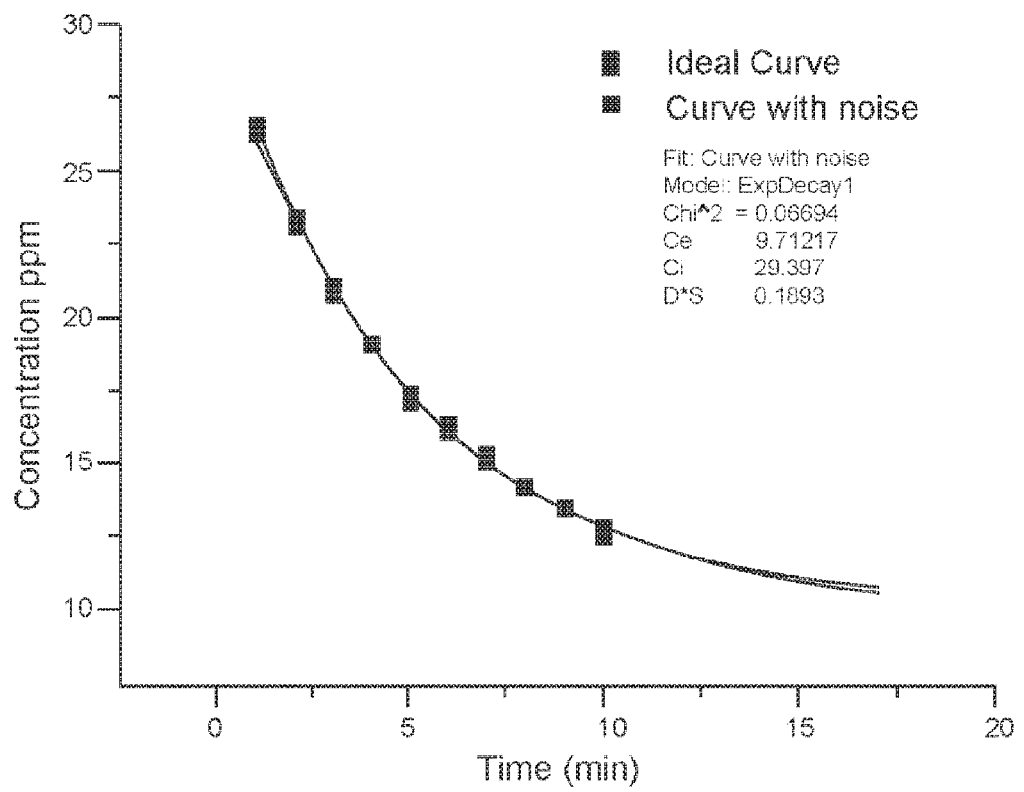
FIG. 6 illustrates a graphical view depicting the concentration of a species versus time.

FIG. 6 is an example of a concentration measurement to calculate effective porosity. For this example, the initial concentration was defined at 30 ppm and the equilibrium concentration at 10 ppm. The exponential constant of diffusion multiplied by the surface area was defined for a 4" cube of cuttings, each with a diameter of 0.25 cm from a well-sorted sand stone reservoir. To this line in the plot, a constant error line of 2% was added. The first line shows the extrapolated curve for the defined situation as compared to the second line which is the extrapolated noisy line. The fit parameters show close agreement with the defined parameters. With an initial reservoir volume of 136 ml, an effective porosity of 0.263 was determined. The defined effective porosity was 0.260. The porosity calculation was completed without the use of the exponential constant. Although the calculation was completed assuming a total volume of a 4" cube, once could monitor the volume of displacement in the reservoir to calculate the bulk volume of cuttings. Because this calculation is independent of surface area, the measurement should only be limited by the accuracy with which the concentrations can be determined.

It is possible the porous medium being tested have an initial concentration of the solute species being monitored. The equation that would apply would be $C_e=(C_I V_R+C_M V_M)/(V_R+V_M)$ where $C_e$ is the equilibrium concentration, $C_I$ is the initial concentration of the reservoir, $V_R$ is the volume of the reservoir, $V_M$ is the volume of the medium and $C_M$ is the initial concentration of the porous medium. This measurement may require a background measurement of the porous medium's fluid content.

The experimental curve shown in FIG. 6 may be more complicated if two types of permeability exist, such as matrix and secondary-fracture, for example. Matrix permeability may be created by the finer grained, interstitial particles that lie between larger particles or in which larger particles are embedded in sedimentary rocks such as sandstones and conglomerates. Secondary fracture permeability may be created by an alteration in the rock. The experimental curve may then be the sum of the two exponential processes. The curve may be modeled as a double exponential. The fit would then yield parameters specific to the matrix permeability, fracture permeability, matrix porosity and fracture porosity.

Returning to FIGS. 1-4, the cuttings or core sample may be removed (23) from the reservoir in order to conduct surface area measurements (25). For a core sample, knowledge of the surface area may be a trivial matter. To determine the surface area of cuttings, a more rigorous approach is usually needed. Various methods may be employed to determine the surface area of a sample (1), such as image analysis, characterization of cuttings based on a repeated sieve cut, measuring the charge buildup on a sample, measuring surface adsorption of a gas onto a solid object or measuring the volume of a thin film of a viscous fluid on the surface of the sample.

Diffusion and permeability both depend on the pore throat and the distance that the detected species travels. Flow of a fluid is proportional to the difference in pressure over a distance with the constant being permeability. Diffusion is proportional to a difference in concentration over a distance with the constant being the diffusion constant. Therefore, the diffusion constant measurements can be used to calculate permeability and porosity information.

Referring to FIG. 5, an apparatus to provide formation measurements by diffusion is shown. A reservoir(33) may be coupled to an injection port (35). In some embodiments, reservoir refers to apart of an apparatus in which a liquid is held. The reservoir may be any shape or size, so long as it is capable of holding a sample (1) and a solution which is capable of diffusing into the sample (1). Injection port may refer to the port in which an element or factor is introduced in or into some situation or subject. The injection port may be automated or be any device or port that allows for introduction of a sample.

The reservoir (33) may be further coupled to a sampler (37). In some embodiments, sampler refers to a device that collects a representative sample for analysis. In another example, sampler (37) refers to a probe that takes continuous or intermittent readings from the reservoir or reservoir headspace. The sampler (37) may also be a probe that can measure concentration continuously or intermittently within the reservoir. An agitator (47) may be positioned adjacent to the reservoir (33). Agitator may refer to a power-driven apparatus for stirring. The agitator may be a magnetic stirring device, for example.

An instrument for analysis (41) may be coupled to the sampler (37). The analysis instrument may be a spectrometer. Further, the analysis instrument may be a laser spectrometer, for example. Optionally, an automatic fluid titrator (39) may be coupled to the reservoir (33). The titrator may be used to adjust salinity, for example. A screen (45) may also be positioned near the bottom of the reservoir (33). In some embodiments, screen refers to a perforated plate, cylinder or similar device or a meshed wire or cloth fabric usually mounted on a frame and used to separate coarser from finer parts or to allow the passage of smaller portions while preventing that of larger. The screen may be used to prevent the sample (1) from coming into contact with the reservoir (33) bottom. A computer (43) may optionally be coupled to any one or combination of the sampler (37), instrument for analysis (41), automatic fluid titrator (39), injection port (35), agitator (47) and reservoir (33). The computer (43) may be utilized to control the parameters of the experiment or to store data derived from experimental procedure.

What is claimed is:

1. A method to determine formation measurements, the method comprising:
   collecting a plurality of formation samples from a subsurface formation that includes a formation fluid;
   analyzing a first formation sample of the plurality to determine a salinity of the first formation sample;
   adding a concentration fluid to a reservoir, wherein the concentration fluid is an isotopic species of a component of the formation fluid;
   sufficiently matching a salinity of the concentration fluid in the reservoir to the salinity of the first formation sample;
   placing a second formation sample of the plurality in the concentration fluid of the reservoir;
   maintaining a salinity of the second formation sample based on placement of a semi-permeable membrane in the reservoir between the concentration fluid and the second formation sample; and
   analyzing the concentration fluid in the reservoir as the second formation sample and fluid equilibrate sufficient to provide diffusion measurements of the second formation sample.

2. The method of claim 1, wherein analyzing the concentration fluid in the reservoir includes removing aliquots from the concentration fluid as the second formation sample and the concentration fluid equilibrate sufficient to provide diffusion measurements.

3. The method of claim 2, further comprising, before removing aliquots, agitating the concentration fluid and the second formation sample in the reservoir.

4. The method of claim 2, wherein the aliquots are liquid samples from the reservoir.

5. The method of claim 2, wherein the aliquots are vapor samples from a headspace of the reservoir.

6. The method of claim 1, further comprising the step of measuring the surface area of the second formation sample, sufficient to provide surface area measurements.

7. The method of claim 6, further comprising the step of calculating formation information from the surface area measurements and diffusion measurements, sufficient to provide porosity and permeability information.

8. The method of claim 1, wherein the concentration fluid further comprises essentially deuterated water.

9. The method of claim 1, wherein the analysis is performed by spectroscopy.

10. A method to determine formation measurements, the method comprising:
    collecting a plurality of formation samples from a subsurface formation that includes a formation fluid;
    analyzing a first formation sample of the plurality to determine a salinity of the first formation sample;
    adding a concentration fluid to a reservoir, wherein the concentration fluid is an isotopic species of a component of the formation fluid;
    sufficiently matching a salinity of the concentration fluid in the reservoir to the salinity of the first formation sample using information about the salinity of the first formation sample;
    placing a second formation sample of the plurality in the concentration fluid of the reservoir;
    maintaining a salinity of the second formation sample based on placement of a semi-permeable membrane in the reservoir between the concentration fluid and the second formation sample;
    analyzing the concentration fluid in the reservoir as the second formation sample and the concentration fluid equilibrate sufficient to provide diffusion measurements;
    measuring the surface area of the second formation sample, sufficient to provide surface area measurements; and
    calculating formation information from the surface area measurements and diffusion measurements, sufficient to provide porosity and permeability information of the second formation sample.

11. The method of claim 10, wherein analyzing the concentration fluid in the reservoir includes removing aliquots from the concentration fluid as the second formation sample and the concentration fluid equilibrate sufficient to provide diffusion measurements.

12. A method to determine formation measurements, the method comprising:

collecting a formation sample from a subsurface formation that includes a formation fluid, wherein the formation sample comprises a plurality of cutting from the subsurface formation;

adding a concentration fluid to a reservoir, wherein the concentration fluid is an isotopic species of a component of the formation fluid;

placing the formation sample in the concentration fluid of the reservoir;

maintaining a salinity of the formation sample based on placement of a semi-permeable membrane in the reservoir between the concentration fluid and the formation sample; and analyzing the concentration fluid as the formation sample and the concentration fluid equilibrate, sufficient to provide diffusion measurements of the formation sample.

13. The method of 12, wherein a headspace of the reservoir is analyzed.

14. The method of claim 12, further comprising before analyzing the concentration fluid, agitating the formation sample in the reservoir.

15. The method of claim 12, further comprising before placing the formation sample in the reservoir, adjusting a salinity in the concentration fluid.

16. The method of claim 12, further comprising the step of measuring the surface area of the formation sample, sufficient to provide surface area measurements.

17. The method of claim 16, further comprising the step of calculating formation information from the surface area measurements and diffusion measurements, sufficient to provide porosity and permeability information.

18. The method of claim 12, wherein the analysis is performed by spectroscopy.

19. The method of claim 18, wherein the analysis if further performed by laser spectroscopy.

20. A method to determine formation measurements, the method comprising:

collecting a plurality of samples from a subsurface formation that includes a formation fluid;

adding a concentration fluid to a reservoir, wherein the concentration fluid is an isotopic species of a component of the formation fluid;

analyzing a first sample of the plurality of samples to determine a salinity of the first sample;

using information about the salinity of the first sample to sufficiently match a salinity of the concentration fluid in the reservoir to a reasonable degree of accuracy;

placing a second sample in the concentration fluid of the reservoir;

maintaining a salinity of the second sample based on placement of a semi-permeable membrane in the reservoir between the concentration fluid and the second sample;

analyzing the concentration fluid of the reservoir as the second sample and concentration fluid equilibrate, sufficient to provide diffusion measurements of the second sample;

measuring the surface area of the second sample, sufficient to provide surface area measurements; and calculating formation information from the surface area measurements and diffusion measurements, sufficient to provide porosity and permeability information of the second sample.

21. A method to determine formation measurements, the method comprising:

collecting a formation sample from a subsurface formation that includes a formation fluid;

adding a concentration fluid to a reservoir, wherein the concentration fluid is an isotopic species of a component of the formation fluid;

adjusting a salinity of the concentration fluid in the reservoir;

placing the formation sample in the reservoir;

maintaining a salinity of the formation sample based on placement of a semi-permeable membrane in the reservoir between the concentration fluid and the formation sample;

analyzing a headspace of the reservoir as the formation sample and the concentration fluid equilibrate, sufficient to provide diffusion measurements of the formation sample;

measuring the surface area of the formation sample, sufficient to provide surface area measurements; and calculating formation information from the surface area measurements and diffusion measurements, sufficient to provide porosity and permeability information of the formation sample.

* * * * *